United States Patent [19]
Sutter

[11] Patent Number: 5,993,446
[45] Date of Patent: Nov. 30, 1999

[54] COAGULATION INSTRUMENT

[75] Inventor: Hermann Sutter, Freiburg, Germany

[73] Assignee: Select Medizin-Technik Herman Sutter GmbH, Freiburg, Germany

[21] Appl. No.: 08/941,780

[22] Filed: Sep. 30, 1997

[30] Foreign Application Priority Data

Oct. 1, 1996 [DE] Germany ............... 196 40 614

[51] Int. Cl.[6] .................................................. A61B 17/39
[52] U.S. Cl. ..................... 606/49; 606/41; 606/48; 606/50; 606/51
[58] Field of Search ................... 606/32, 41–52

[56] References Cited

U.S. PATENT DOCUMENTS

| | | | |
|---|---|---|---|
| 4,483,338 | 11/1984 | Bloom et al. | 606/50 |
| 4,936,842 | 6/1990 | D'Amelio et al. | 606/42 |
| 5,480,409 | 1/1996 | Riza | 606/51 |
| 5,542,945 | 8/1996 | Fritzsch | 606/48 |
| 5,555,618 | 9/1996 | Winkler | 29/825 |
| 5,573,534 | 11/1996 | Stone | 606/48 |
| 5,814,043 | 9/1998 | Shapeton | 606/48 |

FOREIGN PATENT DOCUMENTS 92 09 665 U  11/1992  Germany .

*Primary Examiner*—Linda C. M. Dvorak
*Assistant Examiner*—David M. Ruddy
*Attorney, Agent, or Firm*—Akin, Gump, Strauss, Hauer & Feld, L.L.P.

[57] ABSTRACT

A coagulation instrument has a handle section and detachably connected thereto an electrode shank (4). Electrode conductors (5, 6) are led in the electrode shank from contact pick-off points (7, 8) situated in the direction of the handle to the operating end (9) of the electrode shank. In the region of the contact pick-off points staggered in the longitudinal direction of the electrode shank (4), directly adjacent to the respective internal conductors (5, 6), there is in each case an opening (15) in the insulating outer cover (11). In this region contact sleeves (13, 14) are arranged on the electrode shank and have a depression (16) penetrating the respective opening (15) for contacting the corresponding conductor (5) or (6).

10 Claims, 3 Drawing Sheets

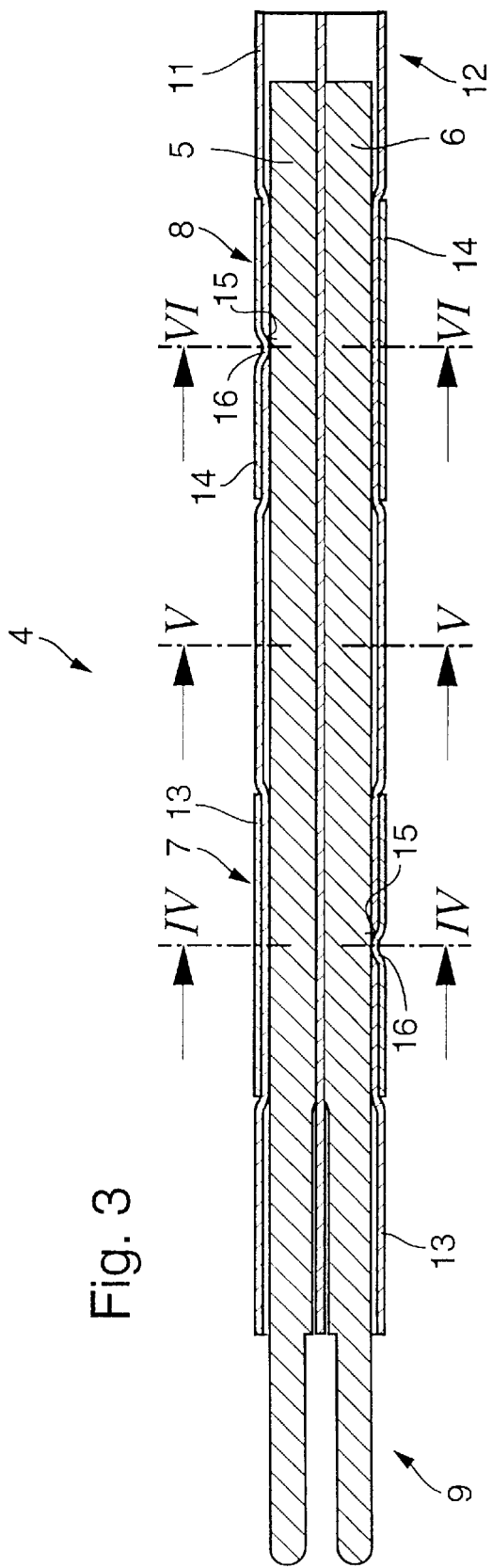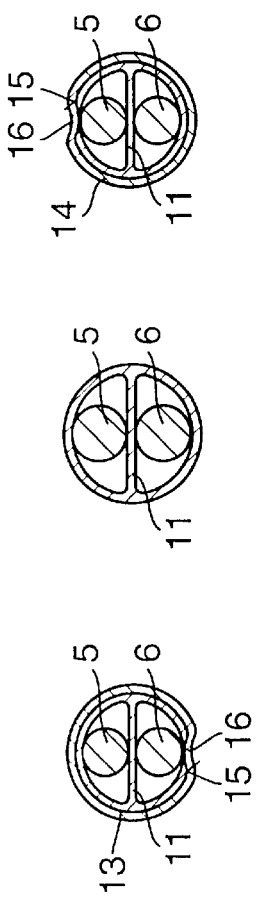

COAGULATION INSTRUMENT

BACKGROUND OF THE INVENTION

The invention relates to a coagulation instrument with a handle section having an electrical connection for a cable as well as including a detachably fittable electrode shank, in which electrode conductors are led from contact pick-off points, which are situated in the direction of the handle and are staggered in the longitudinal direction of the electrode shank, to the operating end of the electrode shank.

In coagulation instruments with detachable electrode shank, the contact pick-off points situated at the handle-end zone are contacted by contact springs situated on the handle section. Plug contacts are provided at the rear end of the handle section and serve for connection to an electric cable. The ends of the electrical conductors or electrode conductors guided within the electrode shank are soldered to the contact pick-off points, whereby the first electrode wire passes to the first contact pick-off point and the second wire passes to the handle-end zone of the electrode shank to the second contact pick-off point. By this means, a mechanical weak point is formed between the first and second contact pick-off point, resulting in an increased risk of rupture. In addition, soldered joints between the electrode wires and the contact pick-off points form electrical weak points.

A further drawback encountered with this prior art is the use of a comparatively large number of component parts, such as insulating intermediate elements, metal turned parts and milled parts, which then also have to be assembled in a time-consuming fashion.

As a result of the complex design of the electrode shank in the connecting area of the electrode wires at the handle-end, this embodiment with electrode shank separable from the handle section is used only where the space conditions still permit such a design. In the case of coagulation instruments having an electrode shank with a diameter of less than about 3 mm, for example in microcoagulation instruments, a one-piece embodiment of electrode shank and handle section is therefore prior art.

SUMMARY OF THE INVENTION

The object underlying the present invention is therefore to provide a coagulation instrument of the type mentioned at the outset with an electrode shank and with an electrode conductor connection in the direction of the handle, which is simple in design, exhibits high mechanical stability and electrical contact stability and can be assembled quickly with little expenditure. In addition, this electrode conductor connection is also to be usable without any difficulty even with very small electrode shank diameters.

To accomplish this object, it is proposed that in the region of the contact pick-off points, directly adjacent to the respective internal conductor, at least one opening is provided in the insulating outer cover of the electrode shank, that in this region of the electrode shank a contact sleeve of at least partly conductive material is placed on the electrode shank and that the contact sleeve has a depression penetrating the opening for contacting the conductor.

Such a conductor connection at the contact pick-off points can be manufactured in an especially simple manner. In particular, no special parts requiring assembly are necessary and vulnerable soldered joints are also avoided.

It is also especially advantageous in this connection that the simple assembly is practically independent of the outside diameter of the electrode shank, so that now very thin, replaceable electrode shanks which are provided with contact pick-off points and have an outside diameter of e.g. two millimeters or even 1 mm are also realizable. Thus, even with such small electrode shank diameters, a two-piece embodiment with separate handle section and detachable electrode shank is possible. This results in a considerable saving of cost, because a single handle section can be used for different electrode shanks or for such with different operating ends. In addition, by virtue of the simple and more economical producibility of the electrode shank according to the invention, there is also the possibility of manufacturing and using the electrode shank as a disposable item.

An advantageous further development of the invention proposes that all the electrical conductors are led together at least to the contact pick-off point closest to the handle, preferably to about the electrode shank end in the direction of the handle.

On the one hand, this measure simplifies the assembly and, in addition, the continuous electrical conductors contribute to the mechanical stabilization. In particular, in this way no weak point between the contact pick-off points is obtained. Finally, the conductor passing over and beyond its connecting point forms a mechanical support in the region of the contact pick-off point situated further in the direction of the handle, such support being effective when the depression contacting the other conductor is made in the contact sleeve or the like.

It is suitable if the electrode conductors are adapted in their cross section approximately to the clear cross section of the respective receiving passage in the electrode shank. Thus the cross section of the electrode shank is at least largely preserved during compression or crimping of the contact sleeve.

If necessary, there is also the possibility that at least in the region of the contact pick-off points there are intermediate elements provided for compensation of different cross sections and/or cross-sectional shapes of the electrical conductors on the one hand and the receiving passages of the electrode shank on the other. By this means there is the possibility that, even with very fine electrode wires, an electrode shank of given outside diameter and then correspondingly large receiving passages be used. Suitable intermediate elements then provide for cross-sectional compensation, so that on the one hand good contact-making is possible and on the other hand there is sufficient stability of the electrode shank. The intermediate elements can extend if necessary over the entire length of the electrode shank and are formed, for instance, by compensating sleeves adapted to be slipped onto the electrical conductors.

The electrode shank is preferably of double-lumen configuration for accommodating the electrode conductors in an insulating fashion, one in each, whereby the electrode conductors preferably take the form of uninsulated wires. Therefore bare wires can be used as electrical conductors, so that stripping measures in the region of the contact pick-off points are not necessary. In addition, in this way larger conductor cross sections can also be used in case of need.

BRIEF DESCRIPTION OF THE SEVERAL VIEWS OF DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3 is an electrode shank represented in longitudinal section;

FIG. 4 is a cross section through the electrode shank shown in FIG. 3, taken along section line IV—IV;

FIG. 5 is a cross-sectional representation of the electrode shank according to FIG. 3, taken along section line V—V; and FIG. 6 is a cross-sectional representation of an electrode shank according to FIG. 3, taken along section line VI—VI.

DETAILED DESCRIPTION OF THE INVENTION

Figure 1:
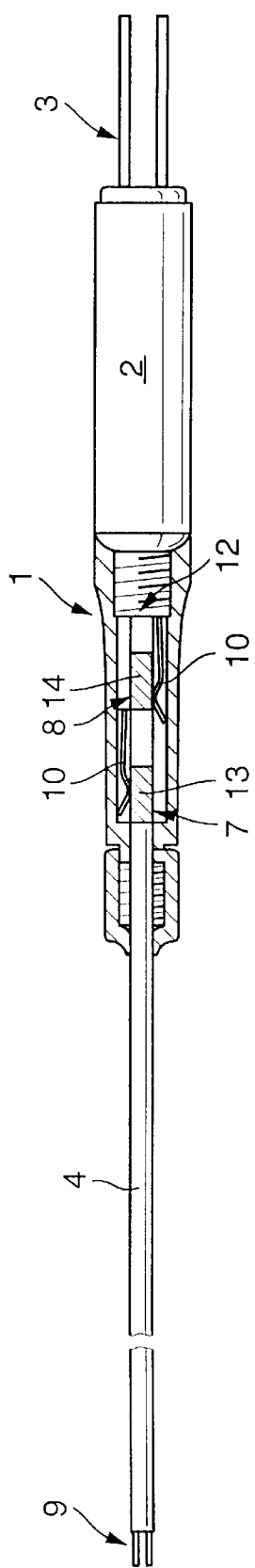
FIG. 1 is a partly sectional side view of a bipolar coagulation instrument.

A bipolar coagulation instrument 1 shown in FIG. 1 has a handle section 2 with an electrical connection 3 for a power cable. An electrode shank 4 is detachably connected to this handle section 2. Electrode conductors 5, 6 (cf. FIG. 3) are led in the electrode shank 4 from contact pick-off points 7, 8 in the direction of the handle to the operating end 9 of the electrode shank 4. For contacting the contact pick-off points 7 and 8 of the electrode shank 4, contact springs 10 are provided at the handle-end and led to the rear, electrical connection 3 of the handle section 2.

The design of the electrode shank 4 according to the invention is to be seen in detail in FIG. 3. The insulating outer cover 11 is of double-lumen configuration for accommodating the electrode conductors (electrical conductors) 5, 6 in an insulating fashion, one in each. It is clearly shown that the two electrode conductors 5 and 6 both pass to the proximity of the handle-end 12 of the electrode shank 4. By this means a uniform mechanical stability of the electrode shank 4 is obtained, to which the electrode conductors 5 and 6 also contribute.

The two contact pick-of points 7 and 8 are arranged in staggered, spaced relationship to each other in the longitudinal direction of the electrode shank and have contact sleeves 13 and 14, respectively. The outer cover 11 has directly adjacent to the respective internal conductor 5, 6 an opening 15 which is penetrated by a depression 16 in the contact sleeves 13, 14 and establishes a conducting connection between the respective electrode conductor 6 or 5 and the contact sleeve 13 or 14.

By means of the contact sleeves 13, 14, circumferentially complete contact pick-off points 7, 8 are formed, so that positioning the electrode shank in the direction of rotation is not necessary during connection to the handle section 2. FIG. 3 also clearly shows that the two contact sleeves 13, 14 are pressed somewhat into the insulating outer cover 11 of the electrode shank 4 and are thereby also additionally located in position against axial movement. Both this pressing and producing the depressions 16 can take place by so-called crimping.

The electrode conductors 5, 6 are preferably configured as solid and plain conductors, so that a high contact stability with the depressions 16, or more specifically with the contact sleeves, is constituted. In addition, it is then not necessary to additionally strip the wires.

FIGS. 4 to 6 show that the cross section of the electrode conductors 5 and 6 is proportioned in such a way that the two diameters of the conductors, with allowance for the intermediate insulation, correspond approximately to the available inside diameter of the electrode shank 4. By this means, especially during crimping, there is adequate support of the two conductors against each other and the cross section of the electrode shank 4 is preserved during compression.

In case of need, the conductor cross sections can also be adapted to the available, free inside cross section of the two receiving lumens in the insulating outer cover. If the electrode shank 4 is to be used for electrodes very small in diameter, there is also the possibility that sleeves as intermediate elements making up for the cross section be slipped onto the electrode conductors. By virtue of the simple design of the electrode shank 4, it presents no problem to realize coagulation instruments with detachable electrode shank of a diameter of, by way of example, only 1 mm.

Figure 2:
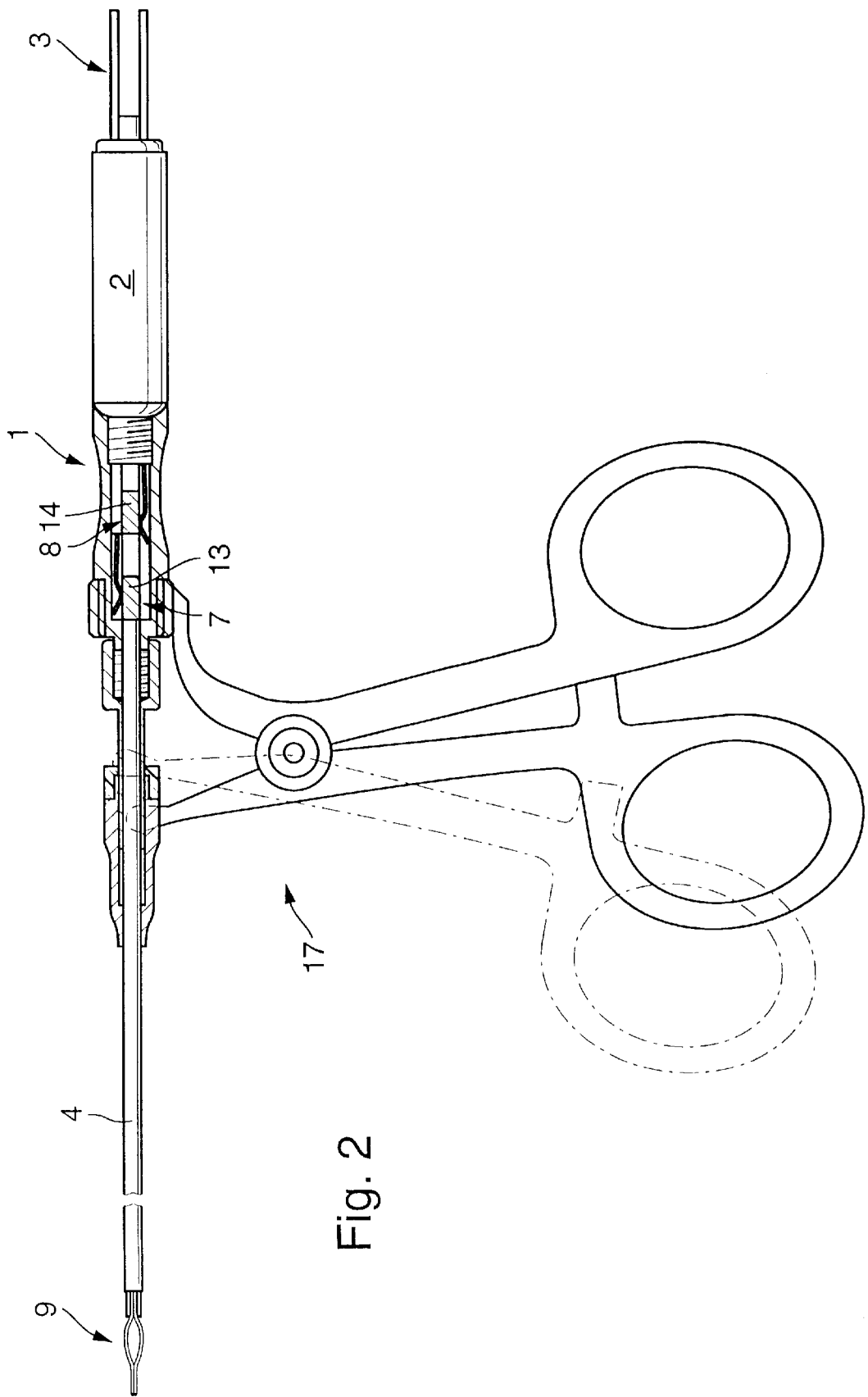
FIG. 2 is a partly sectional side view of bipolar forceps.

FIG. 2 shows another embodiment of a coagulation instrument, whereby here bipolar forceps 17 are shown. The design of the electrode shank 4 and also the contacting within the handle section 2 corresponds in principle to the embodiment according to FIG. 1.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A coagulation instrument (1) having a handle section (2) and an operating end (9), the handle section (2) having an electrical connection (3) for a cable and including a detachably fittable electrode shank (4) in which electrode conductors (5,6) extend from contact pick-off points (7,8), located in proximity to the handle section (2), to the operating end of the electrode shank (4), the contact pickoff points (7,8) being staggered in a longitudinal direction of the electrode shank (4) wherein in a region of the contact pick-off points (7,8), directly adjacent to a respective internal electrode conductor, said electrode shank includes an insulating outer cover (11) having at least one opening (15), in this region of the electrode shank (4), a contact sleeve (13, 14) of at least partly conductive material is placed on the electrode shank, the contact sleeve having a depression (16) that penetrates the at least one opening for contacting one of the electrode conductors.

2. A coagulation instrument as claimed in claim 1, wherein the electrode conductors (5,6) are led together at least to a contact pick-off point (8) closest to the handle section (2).

3. A coagulation instrument as claimed in claim 2, wherein the electrode conductors (5,6) are electrically connected to an electrode shank end (12) closest to the handle section (2).

4. A coagulation instrument as claimed in claim 1, wherein the electrode shank (4) is formed as one piece with the insulating outer cover (11) with two lumens for accommodating the electrode conductors (5,6) in an insulating fashion, one conductor in each lumen, each electrode conductor being an uninsulated wire.

5. A coagulation instrument as claimed in claim 1, wherein in case of two electrode conductors (5,6) in the electrode shank (4), the at least one opening in the electrode shank-wall for contacting the electrode conductors comprises two openings which are provided at approximately diametrically opposed sides of the electrode shank (4) for connecting the electrode conductors with respective contact sleeves (13, 14).

6. A coagulation instrument as claimed in claim 1, wherein the electrode conductors (5,6) have cross sections approximately equal to cross sections of respective receiving passages in the electrode shank (4).

7. A coagulation instrument as claimed in claim 6, wherein at least in the region of the contact pick-off points (7,8) there are intermediate elements provided for compensation of different cross sections and/or cross-sectional shapes of the electrical conductors and the receiving passages of the electrode shank (4).

8. A coagulation instrument as claimed in claim 1, wherein the contact sleeves (13, 14) are fixed on the electrode shaft (4) by pressing or crimping.

9. A coagulation instrument as claimed in claim 1, wherein the electrode shank (4) has an outside diameter of less than about 4 mm.

10. A coagulation instrument as claimed in claim 9, wherein the outside diameter is less than about 3 mm.

* * * * *